United States Patent [19]

Carduck et al.

[11] Patent Number: 4,954,664
[45] Date of Patent: Sep. 4, 1990

[54] PROCESS FOR THE DIRECT HYDROGENATION OF BUTTERFAT

[75] Inventors: Franz-Josef Carduck, Haan; Juergen Falbe, Neuss; Theo Fleckenstein, Hilden; Gerd Goebel, Erkrath; Joachim Pohl, Duesseldorf, all of Fed. Rep. of Germany

[73] Assignee: Henkel Kommanditgesellschaft auf Aktien, Duesseldorf, Fed. Rep. of Germany

[21] Appl. No.: 470,428

[22] Filed: Jan. 25, 1990

Related U.S. Application Data

[63] Continuation of Ser. No. 166,956, Mar. 11, 1988, abandoned.

[30] Foreign Application Priority Data

Mar. 16, 1987 [DE] Fed. Rep. of Germany ....... 3708430

[51] Int. Cl.$^5$ .............................................. C07C 27/00
[52] U.S. Cl. ..................................... 568/864; 568/855
[58] Field of Search .................................. 568/864, 885

[56] References Cited

U.S. PATENT DOCUMENTS

| 74,814 | 0/1868 | Carduck et al. | |
| 3,173,959 | 3/1965 | Rittmeister | 260/638 |
| 3,193,586 | 7/1965 | Rittmeister | 260/638 |

FOREIGN PATENT DOCUMENTS

| 2513377 | 1/1977 | Fed. Rep. of Germany . |
| 2613226 | 12/1978 | Fed. Rep. of Germany . |

*Primary Examiner*—Bruce Gray
*Attorney, Agent, or Firm*—Ernest G. Szoke; Wayne C. Jaeschke; Daniel S. Ortiz

[57] ABSTRACT

A process for the catalytic hydrogenation of butterfat where non-deacidified butterfat is continuously reacted with hydrogen under pressures of from 20 to 300 bar and at temperatures of from 180° to 250° C. with molar ratios of hydrogen to fatty acid residue in the butterfat of from 10:1 to 500:1. The reaction is carried out over catalysts which contain from 30 to 40% by weight copper, from 23 to 30% by weight chromium, from 1 to 10% by weight manganese, from 1 to 10% by weight silicon, and from 1 to 7% by weight barium. The percentages by weight in each case are based on the total oxidic mass of the catalyst. Other transition metals, especially zirconium and cerium, are additionally incorporated into the catalyst. The metals in the catalyst are converted to their oxides by calcination. The catalyst is converted into shaped particulate or granulated elements with from 1 to 10% by weight of at least one binder in addition to 1 to 10% by weight graphite. The catalyst is activated with hydrogen or a hydrogen-containing gas mixture.

The reaction products include alcohols, oxo- and hydroxyfatty alcohols corresponding to the natural fatty acid composition of the butterfat and the desired, valuable product, propylene glycol. This process is advantageous since it eliminates the need for preseparation of the relatively short-chain fatty acids (or deacidification) of the butterfat prior to hydrogenation.

21 Claims, No Drawings

PROCESS FOR THE DIRECT HYDROGENATION OF BUTTERFAT

This application is a continuation, of application Ser. No. 07/166,956, filed 03/11/88.

BACKGROUND OF THE INVENTION

1. Field of the Invention

This invention relates to a new process for the direct catalytic hydrogenation of butterfat without preliminary separation of short-chain fatty acids using particulate and/or granulated catalysts containing copper chromite.

2. Statement of Related Art

Fatty alcohols, which are predominantly linear, monofunctional alcohols having chain lengths of 8 or more carbon atoms, and their production are described in detail in the literature (Ullmanns Encyklopädie der technischen Chemie, 4th Edition, Vol. 11, pages 427 to 445). A preferred starting material for their production are the fatty acids and fatty acid mixtures occurring in natural fats and/or oils which may be converted into fatty alcohols of corresponding chain length by catalytic hydrogenation. Through the use of the methyl esters of the fatty acids rather than the free fatty acids, themselves, the catalysts are protected against aggressive attack by the free carboxyl group. This enables industrial processes to be operated for sufficiently long periods with satisfactory volume-time yields. Today, therefore, the predominant quantity of native fatty alcohols is produced from fatty acid methyl esters by the gas-phase hydrogenation process in which the distilled methyl esters are passed in the vapor phase together with a large excess of hydrogen over a fixed bed of copper-containing mixed oxide catalysts such as, for example, copper chromite spinel catalysts. Temperatures above 200° C. and under pressures of from about 250 to 300 bar are useful.

Copper-mixed oxide catalysts obtained by co-precipitation via the wet route are used as particulate catalysts or extrudates. Before use the catalysts are generally reduced in the plant or installation.

Fatty acid esters, especially fatty acid methyl esters, and free fatty acids are used simultaneously as starting materials for the hydrogenation reaction to saturated and/or unsaturated fatty alcohols according to the patent literature, for example, U.S. Pat. Nos. 3,193,586, 3,173,959, and German Patent Nos. 2,513,377 and 2,613,226.

By virtue of its fatty acid composition, butter is a tallow substitute. By melting out butter, separating off the aqueous phase and heating to 100° to 105° C., it is possible to obtain clarified or run butter which is 99.3% butterfat containing at most 0.5% water and hardly any lactose, casein or salts (Römpp's Chemie Lexikon, 8th Edition, page 544. Butterfat is defined in the prior art as the oily portion of mammals milk composed of 88% of the glycerides of oleic, stearic, and palmitic acids, and 6% of the glycerides of butyric, caproic, caprylic and capric acids (HACKH's Chemical Dictionary, 4th Edition, page 117).

In the conventional processing of butter or butterfat, process-related difficulties are encountered both during the transesterification step and during the fat splitting step on account of the high proportion of short-chain fatty acids containing from 4 to 10 carbon atoms. These difficulties lead to uneconomical hydrogenation processes. The short-chain fatty acids are normally separated off as methyl esters. In this case, just as in processing by fat splitting, unpleasant odors are emitted by the short-chain fatty acids. In addition the high solubility of the fatty acids in the water of the splitting reaction presents practical problems.

Further problems arise in the separation of the methanol from the short-chain fatty acids because the boiling points partly overlap so that some of the methanol is lost during working up.

Co-pending application U.S.S.N. 074,814, filed July 17, 1987, describes subject matter which is related to the present invention.

DESCRIPTION OF THE INVENTION

Other than in the operating examples, or where otherwise indicated, all numbers expressing quantities of ingredients or reaction conditions used herein are to be understood as modified in all instances by the term "about".

An object of the present invention is to provide a process for the direct catalytic hydrogenation of butterfat without preliminary separation of the relatively short-chain fatty acid (non-deacidified butterfat) using particulate and/or granulated catalysts containing copper chromite, which obtains high yields of the valuable product, propylene glycol, and the fatty alcohols, oxo- and hyroxyfatty alcohols corresponding to the natural fatty acid composition.

The heterogenous transition metal catalyst used for the reaction is highly active and selective and leads to the desired products, particularly propylene glycol, without secondary reactions contributing significantly to a reduction in the product yield. This improves the economy of the process in relation to the prior art.

It has now surprisingly been found that it is possible with certain highly active and selective, long-life catalysts containing copper chromite as principal constituent to control the direct hydrogenation of non-deacidified butterfat to fatty alcohols and propylene glycol in such a way that the formation of hydrocarbons is largely suppressed. At the same time the valuable product, propylene glycol, is obtained in a high yield.

The present invention relates to a process for the direct catalytic hydrogenation of butterfat without preliminary separation of short-chain fatty acids at high reaction temperatures using particulate and/or granulated catalysts containing copper chromite as principal constituent to fatty alcohols, oxo- and hydroxyfatty alcohols corresponding to the natural fatty acid composition and propylene glycol. According to the present invention, non-deacidified butterfat is continously reacted with hydrogen under presssures of from 20 to 300 bar and at temperatures of from 180° to 250° C. with molar ratios of hydrogen to fatty acid residues in the butterfat of from 10 : 1 to 500 : 1. The reaction is carried out in the presence of a catalyst which contains from 30 to 40% by weight copper, from 23 to 30% by weight chromium, from 1 to 10% by weight manganese, from 1 to 10% by weight $SiO_2$ and from 1 to 7% by weight barium (% by weight, based in each case on oxidic catalyst mass). If desired, other transition metals are employed in the form of their oxides.

The catalyst is calcined by known methods, converted into shaped particulate and/or coarse-grained elements with from 1 to 10% by weight, based on oxidic catalyst, of at least one binder in addition to 1 to 10% by weight graphite, and activated with hydrogen or a hydrogen-containing gas mixture.

In one preferred embodiment, the hydrogenation reaction is carried out under a pressure of from 100 to 300 bar.

The starting material used for the hydrogenation process according to the invention is butter containing mono- or polyunsaturated fatty acids esterified with glycerol. The fatty acid residues may have the same or different degrees of saturation and alkyl chain lengths.

After preliminary purification, dehydration and desulfurization, butter or butterfat is reacted as a triglyceride with hydrogen in a trickle-bed reactor containing a fixed bed of catalyst. A mixture of fatty alcohols, oxo- and hydroxyfatty alcohols to the natural fatty acid composition is obtained as the reaction product. Unsaturated C-C-double bonds are saturated. Propylene glycol is formed from the bound glycerol with elimination of water. The conversion is 99%.

The hydrogenation effluent is a colorless, clear liquid (without the typical rancid odor) which is dried by known methods and then freed from low-boiling constituents.

The product mixture is then separated by distillation into a head fraction ($C_4$–$C_{10}$), a main fraction ($C_{12}$–$C_{18}$), and a residue. A portion of the residue may be recycled.

The main fraction substantially corresponds in its C-chain distribution to the composition of tallow fatty alcohol, i.e, fatty alcohols essentially containing 14, 16 and 18 carbon atoms.

To separate off the propylene glycol, the head fraction is extracted with water and worked up by distillation.

An advantage of the present invention is that butterfat is hydrogenated directly thereby avoiding the transesterification step or fat splitting of butterfat. This eliminates the need to separate off the fractions in the butter of approximately 10% of $C_4$–$C_{10}$ fatty acids in the form of the methyl ester or as free fatty acid. In addition, where the process of the present invention is employed, there is no longer any need for the elaborate purification process required for the separation of methanol in the hydrogenation of methyl ester. Unpleasant odors emitted during processing by fat splitting are avoided as well as any problems attributable to the high solubility of the short-chain fatty acids in the water of the splitting reaction. In addition, the valuable product, propylene glycol, is obained in a high yeild.

In one preferred embodiment of the process according to the invention, butterfat is continuously hydrogenated using a catalyst advantageously containing from 32 to 38% by weight copper, based on the oxidic catalyst mass. It can also be of advantage to adjust the quantity of chromium in the catalyst used to a range of from 26 to 29% by weight, the quantity of manganese to a range of from 1 to 6% by weight, the quantity of barium to a range of from 1.5 to 3% by weight, and the quantity of silicon to a range of from 1.5 to 3% by weight, based in each case on the oxidic catalyst mass before activation. In one particularly preferred embodiment, a catalyst containing 36% by weight copper, 29% by weight chromium, 2.5% by weight manganese, 1.7% by weight barium, and 1.0% by weight silicon, based in each case on the oxidic catalyst mass before activation, in the form of their oxides is used for the direct catalytic hydrogenation of butterfat. With catalysts such as described herein, it is possible to obtain considerable increases in activity. For this reason, the use of such catalysts in the process according to the invention is regarded as particularly preferred.

In another preferred embodiment of the process according to the invention, a catalyst containing other transition metals in the form of their oxides in addition to the above-mentioned quantities of copper, chromium, manganese, barium and silicon is used for the direct catalytic hydrogenation of butterfat. A catalyst is employed containing from 1 to 5% by weight and, preferably, from 2 to 3% by weight each of zirconium and/or cerium in addition to the metals mentioned. In this connection, it is useful to add one of the transition metals mentioned in the form of its oxides or even several of the transition metals mentioned in the form of their oxides in admixture with one another to the catalysts used in accordance with the invention. The use of additionally doped catalysts such as described herein the process according to the invention leads to a considerable increase in the activity and selectivity of the catalyst in relation to the yield of propylene glycol, particularly where hydrogenation is carried out in a trickling bed.

Catalysts according to the invention optionally contain from 1 to 10% by weight of graphite to improve the processing of the granulates and/or extrudates. A quantity of 5% by weight of graphite is preferably added to and thoroughly mixed with the calcined powder-form material before granulation.

According to the invention, an improvement in the process was obtained by bringing the catalyst used containing the above-mentioned metals in the form of their oxides and graphite into granulate or extrudate form using from 1 to 10% by weight of one or more binders and preferably 10% by weight of one or more binders. Suitable binders are compounds known for this purpose from the prior art, of which either one or even several may be used in the catalyst used in accordance with the invention. The use of one or more binders selected from the group consisting of polyvinyl acetate and methylmethacrylate has proved to be particularly effective. In contrast to numerous, non-free-flowing catalyst materials known from the prior art, it was possible to provide a catalyst in granulate or extrudate form for the process according to the invention, of which the loosened, porous structure contributes significantly to increasing the activity and selectivity of the catalyst in the direct hydrogenation of butterfat, particularly in a trickling bed. Polyvinyl acetate is preferably used as binder for the production of the catalyst granulates or extrudates commercially obtainable 40% by weight polyvinyl acetate suspensions, for example, being used for the production of the catalyst. After thorough mixing, polyvinyl acetate suspensions are added in small quantities to the calcined, powder-form catalyst materials and mixed therewith until agglomerate grains begin to build up. The agglomerate-containing powder is then compacted to small granulates, for example in a perforated-roll granulator, this process being known from the prior art. The granulates are dried in a known manner to residual moisture contents of from 10 to 15%. The granulates resulting from this operation are sieved, grain fractions of a certain grain size being sieved out for the process according to the invention. Catalyst grain fractions having a grain size of from 0.6 to 3 mm are advantageously used where the process according to the invention is used for the catalytic hydrogenation of fatty acid methyl ester mixtures.

The catalysts can be compressed into tablet form, for example, into 4×4 mm tablets. For hardening, the tablets are tempered in air for 6 hours at a temperature of 200° C. The specifiC surface as determined by the BET method (Z. Anal. Chem. 238 (1968), 187–193) was 40±10 m²/g.

The granulated catalysts suitable for use in the process according to the invention for the direct hydrogenation of butterfat have a specific surface of from 30 to 50 m²/g. The described form of pregranulation leads to a special, loosened pore structure which increases the degree of pore utilization.

In the course of the studies leading to the process according to the invention for the direct hydrogenation of butterfat, it was found to be of particular advantage to react butterfat with hydrogen in the presence of a catalyst of which the granulates of extrudates have a diameter of from 1 to 6 mm and a length of from 1 to 6 mm. Granulates or extrudates (tablets) such as these show excellent activity and selectivity in the direct reaction of butterfat with hydrogen and, in addition, may readily be separated from the reaction products. In addition, the useful lives obtainable with these catalysts are considerably better than the useful lives of the catalysts known from the prior art which had the disadvantage that, in some cases, they disintegrated during the reaction and as a result could only be separated from the reaction products with considerable difficulty.

Another factor significantly affecting the activity and selectivity of the catalysts used in accordance with the invention is the pore volume of the shaped catalyst elements. It has been found that the pore volume of the catalysts useable in accordance with the invention must lie in an optimal range to produce optimal results. In one preferred embodiment of the process according to the invention, metal-containing catalysts are used of which the pore volume is in the range of from 0.4 to 0.6 cm³/g. A pore volume in this range also has the advantage of contributing towards increasing the activity and selectivity of the hydrogenation catalysts. High activities and selectivities may be obtained both in trickling bed reactors and in sump phase reactors. At the same time, such catalysts had an extremely long useful life in the process according to the invention and did not present any problems during the separation of catalyst and reaction products.

The catalysts used in the process according to the invention are normally activated with hydrogen or with a hydrogen-containing gas mixture before they are used. For economic reasons, a gas mixture predominantly consisting of a nitrogen/hydrogen gas mixture is advantageously used for activation of the catalyst mass. As known from the prior art, such activation may advantageously be carried out by drying the catalyst mass in a stream of nitrogen at elevated temperature after their production and adding hydrogen in increasing quantities to the drying gas for activation. The proportion of hydrogen in the activating gas mixture can be between 0.1 and 10% by volume. The activation of the catalysts may be carried out both in situ and also in vessels separate from the reaction vessel.

The reaction temperatures in the direct hydrogenation of butterfat in accordance with the present invention are in the range from 180° to 250° C. and, preferably, in the range from 200° to 240° C. In the temperature control of the reaction, a general factor to be taken into consideration is that the hydrogenation to corresponding fatty alcohols, oxo- and hydroxyfatty alcohols corresponding to the natural fatty acid composition is an exothermic chemical reaction. Accordingly, in the control of the reaction temperature, it is important to ensure that, after the reduction of the glyceride oils has "started", the heat of reaction generated is dissipated in the usual way.

The process according to the invention for the direct hydrogenation of butterfat is also characterized in that the molar ratio of hydrogen to fatty acid residue in the butterfat substrate is adjusted to a value of from 10:1 to 500:1. This means that the throughput of hydrogen gas, as measured in moles/hour, is from 10 to 500 times higher than the throughput of butterfat, as measured in moles fatty acid residue/hour.

Advantages of the process according to the invention include simplification of the production of fatty alcohols through optimization both of the chemical composition and of the physical composition of the copper chromite catalysts which are used. In contrast to prior processes where fatty acid methyl esters are hydrogenated as a first step, there is no longer any need for the elaborate separation of methanol from short-chain fatty acid methyl esters.

The use of the catalyst according to this invention in conjunction with the described procedure provides for the production of fatty alcohols, oxo- and hydroxyfatty alcohols corresponding to the natural fatty acid composition of butterfat without any need for the short-chain fatty acids to be separated off beforehand. In addition, propylene glycol is obtained as a valuable secondary product.

The invention is illustrated by the following Examples but is not limited thereby.

EXAMPLE 1

Catalyst preparation 84.93 g Ba(NO$_3$)$_2$, 3493 g Cu(NO$_3$)$_2$ . 2 H$_2$O, 294.43 g Mn(NO$_3$)$_2$ . 4 H$_2$O and 62.3 g SiO$_2$ in the form of a 40% by weight silica sol were dissolved with vigorous stirring in 9 liters deionized water at temperatures of from 30° to 90° C. In a second vessel, 1639 g CrO$_3$ were dissolved in 9 liters deionized water under the same conditions, followed by the addition of 3650 g of a 25% ammonia solution. The solution containing barium, manganese and copper was then pumped at 30° to 90° C. into the ammonium chromate solution, a mixture of barium chromate, manganese hydroxide, silicon hdroxide and copper chromate being precipitated from the solution. Precipitation stopped when the pH value fell below 7.

The precipitate was filtered in a frame filter press and washed with deionized water until free from nitrate. The filter cake was dried overnight at 90° to 120° C. and then reduced to a coarse powder in a cutting mill. The resulting chromate powder was thermally decomposed ("calcined") to chromite at 300° to 500° C. in a revolving tubular furnace. The calcined powder-form material had the following chemical composition:

Cu: 38±0.5%
Cr: 29±0.5%
Mn: 2.5±0.5%
Ba: 1.9±0.5% and
Si: 1±0.3%.

5% by weight graphite was added to 1 liter of the powder, followed by mixing for 15 minutes in a Lödige mixer. 10% by weight of a 40% by weight polyvinyl acetate suspension was then added, followed by brief mixing until agglomerates began to build up. The powder was then compacted to small granulates in a perforated-roll granulator, dried to a residual moisture content of 10 to 15% and sieved to a 0.6 to 3 mm grain fraction.

The powder had excellent flow properties and could be compressed in a rotary tabletting machine to tablets 3 to 6 mm diameter and 2 to 4 mm thick.

After hardening of the tablets (6 hours, 200° C. in air), the specific BET surface was 40±10 m²/g for a pore volume of from 0.4 to 0.6 cm³/g.

Preparation of the hydrogenation product

Unsalted German branded butter was used as starting material. The butter was melted and the triglycerides separated from water and an emulsion phase.

0.5 liter of the catalyst prepared as set forth above and granulated (mean grain size 1 mm) was introduced into a reaction tube 1 liter in volume with an internal diameter of 25 mm to which 2 mm glass beads were then added in order uniformly to disperse the liquid phase.

After drying and reduction of the catalyst in a stream of nitrogen/hydrogen (max. hydrogen concentration 1%; max. temperature 200° C.), hydrogen was continuously passed downwards through the reactor co-current with butterfat. The liquid, clear reaction product which solidified at room temperature was collected in a separation system. The reaction conditions and the product analysis were as follows:

| Test Results | |
|---|---|
| Pressure: 250 bar | Acid value (a.v.) = 0.6 |
| Sulfur content: 16 ppm | |
| Reaction temperature (°C.) | 220 |
| LHSV* (1 × 1⁻¹ × 1⁻¹) | 1.0 |
| Hydrogen throughput (Nm³/h) | 10 |
| Saponification value of product | 1.0 |

*LHSV = liquid hourly space velocity

The analysis of the C-chain distribution of the fatty acids was as follows:

| C 4 | 3.2% | C 16/1 | 1.5% |
|---|---|---|---|
| C 6 | 2.7% | C 17 | 0.5% |
| C 8 | 1.4% | C 18 | 10.0% |
| C 10 | 3.0% | C 18/1 | 23.1% |
| C 12 | 3.8% | C 18/2 | 1.4% |
| C 14 | 11.0% | C 18/3 | 1.2% |
| C 15 | 1.1% | | |
| C 16 | 27.6% | unidentified compounds* | 8.5% |
| | | Total | 100% |

*The unidentified compounds consisted predominantly of not further characterized branched fatty acids In the data set out above, where a number succeeds the chain length, this refers to the number of double bonds in the molecule, e.g., C18/2 indicates two double bonds.

A colorless clear hydrogenation effluent was obtained which solidified at room temperature. The saponification at room temperature was obtained. The saponification values were below 1.0.

In addition to the hardened fatty alcohols, 8% propylene glycol (corresponding to 86% of the theoretical) and 0.19% hydrocarbons were obtained.

EXAMPLE 2

The starting material used was butterfat (99.8%) obtained by pretreatment for 0.5 hour at 90° C. with Fuller's earth/activated carbon (2% of a mixture of Floridin and 10% activated carbon).

The tests were carried out as in Example 1 in a 0.5 liter volume trickling bed reactor; after melting and heating to the reaction temperature, butterfat was passed downwards to the reaction temperature, butterfat was passed downwards through the reactor in co-current flow with preheated hydrogen.

Characteristic data of the starting product
acid value (a.v.): 1.2
Saponification value (s.v.): 234
Iodine value (i.v.): 29.3
Sulfur content: <4 ppm

| C-chain distribution: | | | |
|---|---|---|---|
| C 4 | 1.4% | C 16 | 22.8% |
| C 6 | 2.8% | C 16:1 | 7.1% |
| C 8 | 2.1% | C 18 | 7.2% |
| C 10 | 4.7% | C 18:1 | 17.8% |
| C 12 | 4.7% | C 18:2 | 3.6% |
| C 14 | 12.75% | unidentified | 11.95% |
| C 15 | 1.1% | compounds* | |
| | | Total | 100% |

*see Example 1

Reaction conditions:
Temperature 200° C.
Pressure 250 bar
LHSV 1×1⁻¹×1⁻¹
Hydrogen/substrate=200:1 (mole/mole equivalent)
Reaction product:
Water-clear hydrogenation effluent

| Characteristic data: s.v.: | 0.4 |
|---|---|
| a.v.: | <0.5 |
| i.v.: | <1 |
| Fatty alcohol content: | 87.0% |
| Propylene glycol: | 8.6% |
| Hydrocarbons: | 0.01% |

EXAMPLE 3

The same butterfat starting product as in Example 2 was hydrogenated at a reaction temperature of 195° C., but under otherwise the same conditions A water-clear hydrogeneration effluent again was obtained.

| Characteristic data: | s.v. = | 1.0 |
|---|---|---|
| | a.v. = | <0.5 |
| | i.v. = | <1 |
| Fatty alcohol content: | | 86.9% |
| Propylene glycol: | | 9.0% |
| Hydrocarbons: | | 0.01% |

We claim:
1. A process for the direct catalytic hydrogenation of butterfat which comprises:
A. continuously reacting non-deacidified butterfat with hydrogen under pressures of from about 20 to about 300 bar and at temperatures of from about 180° to about 250° C. with molar ratios of hydrogen to fatty acid residues in the butterfat of from about 10 : 1 to about 500 : 1, the reaction being carried out in the presence of a catalyst which contains from about 30 to about 40% by weight copper, from about 23 to about 30% by weight chromium, from about 1 to about 10% by weight manganese, from about 1 to about 10% weight silicon and from about 1 to about 7% by weight barium, the percentages by weight being based on the total weight of the catalyst, to form a reaction product containing fatty alcohols, oxo- and hydroxyfatty alcohols corresponding to the butterfat composition and propylene glycol, and;

B. separating the reaction products from residue.

2. The process of claim 1 wherein the catalyst additionally contains from about 1 to about 10% by weight or at least one binder and from about 1 to about 10% by weight graphite, and is in the form of shaped particulates or granulates.

3. The process of claim 1 wherein the catalyst is activated with hydrogen or a hydrogen containing gas.

4. The process of claim 1 wherein the hydrogenation is carried out at a pressure from about 100 to about 300 bar.

5. The process of claim 1 wherein the catalyst contains from about 32 to about 38% by weight copper.

6. The process of claim 1 wherein the catalyst contains from about 26 to 29% by weight chromium.

7. The process of claim 1 wherein the catalyst contains from about 1.5% to about 3% by weight barium.

8. The process of claim 1 wherein the catalyst contains from about 1.5 to about 3% by weight silicon.

9. The process of claim 1 wherein the cataylst contains from about 1 to about 6% by weight manganese.

10. The process of claim 1 wherein the catalyst additionally contains from about 1 to about 5% by weight of at least one of zirconium cerium.

11. The process of claim 1 wherein the catalyst additionally contains from about 2 to about 3% of at least one of zirconium and cerium.

12. The process of claim 1 wherein the catalyst contains from about 32 to about 38% by weight copper, from about 26 to about 29% by weight chromium, from about 1 to about 6% by weight manganese, from about 1.5 to about 3% by weight barium, from about 1.5 to about 3% by weight silicon and from about 1 to about 5% by weight of at least one of zirconium or cerium.

13. The process of claim 1 wherein the catalyst contains from about 1 to about 10% by weight of a binder selected from the group consisting of polyvinyl acetate and methyl methacrylate.

14. The process of claim 1 wherein the catalyst has a grain size of from about 0.6 to about 3 mm.

15. The process of claim 2 wherein the particulates or granulates have a diameter of from 1 to 6 mm and a length of from 1 to 6 mm.

16. The process of claim 1 wherein the catalyst has a specific surface of from about 30 to about 50 $m^2/g$.

17. The process of claim 1 wherein the catalyst has a pore volume of from about 0.4 to about 0.6 $cm^3/g$.

18. The process of claim 1 wherein the catalyst is activated with an $N_2/H_2$ gas mixture containing from about 0.1 to about 10% by volume hydrogen.

19. The process of claims 1 wherein reaction temperatures are between about 200° to about 240° C.

20. The process of claim 1 wherein the reaction product is separated by distillations into a head fraction containing $C_4$ to $C_{10}$ components and propylene glycol, a main fraction containing $C_{12}$ to $C_{18}$ components, and a residue.

21. The process of claims 20 wherein the propylene glycol is separated from the $C_4$ to $C_{10}$ head fraction.

* * * * *

UNITED STATES PATENT AND TRADEMARK OFFICE
CERTIFICATE OF CORRECTION

PATENT NO. : 4,954,664
DATED : September 4, 1990
INVENTOR(S) : Carduck et al.

It is certified that error appears in the above-identified patent and that said Letters Patent is hereby corrected as shown below:

In Claim 2, Column 9, Line 11, "or" should read --of--.

IN Claim 10, Column 9, Line 31, insert --and-- after"zirconium".

Signed and Sealed this

Twenty-eighth Day of April, 1992

Attest:

HARRY F. MANBECK, JR.

*Attesting Officer*  *Commissioner of Patents and Trademarks*